(12) United States Patent
Currie et al.

(10) Patent No.: US 11,740,168 B2
(45) Date of Patent: Aug. 29, 2023

(54) QUALITY INSPECTION TOOL FOR PROJECTION WELDED FASTENERS

(71) Applicant: Volvo Car Corporation, Gothenburg (SE)

(72) Inventors: Martin Currie, Gothenburg (SE); Leif Winberg, Gothenburg (SE); Hans Lundberg, Gothenburg (SE)

(73) Assignee: Volvo Car Corporation, Gothenburg (SE)

( * ) Notice: Subject to any disclaimer, the term of this patent is extended or adjusted under 35 U.S.C. 154(b) by 568 days.

(21) Appl. No.: 16/871,100

(22) Filed: May 11, 2020

(65) Prior Publication Data

US 2021/0348997 A1 Nov. 11, 2021

(51) Int. Cl.
| | |
|---|---|
| *G01N 3/307* | (2006.01) |
| *G01N 3/02* | (2006.01) |
| *G01N 33/207* | (2019.01) |
| *G01N 3/62* | (2006.01) |

(52) U.S. Cl.
CPC ............... *G01N 3/307* (2013.01); *G01N 3/02* (2013.01); *G01N 3/62* (2013.01); *G01N 33/207* (2019.01); *G01N 2203/001* (2013.01); *G01N 2203/0014* (2013.01); *G01N 2203/0035* (2013.01)

(58) Field of Classification Search
CPC ...... G01N 3/307; G01N 3/48; G01R 1/06722; G01B 7/30; G01B 7/001; G06Q 90/00; F16B 21/088; B23P 19/06; A61M 5/2033; B25B 23/0078; B25B 13/08; A62B 3/005; G21C 19/10; H01H 21/10; B25D 17/06
See application file for complete search history.

(56) References Cited

U.S. PATENT DOCUMENTS 3,956,843 A * 5/1976 Litman ................... F41A 21/28
                                                   42/105
4,640,119 A * 2/1987 Ludwig ................... G01N 3/48
                                                  173/202

(Continued)

FOREIGN PATENT DOCUMENTS

| CN | 201788117 U | 4/2011 |
|---|---|---|
| CN | 201844954 U | 5/2011 |
| CN | 102494947 A | 6/2012 |

(Continued)

*Primary Examiner* — Brandi N Hopkins
(74) *Attorney, Agent, or Firm* — Clements Bernard Walker; Christopher L. Bernard

(57) ABSTRACT

A handheld quality inspection tool for projection welded components and method for utilizing the same is disclosed. The handheld quality inspection tool includes an elongated hollow tube, a spring support, a spring member, a plunger, and a handle. The elongated hollow tube defines a slot. The spring support is connected to an end portion of the elongated tube. The spring member is disposed within the elongated hollow tube and connected to the spring support. The plunger is disposed in the elongated hollow tube and connected to the spring member opposite the spring support. The handle is connected to the plunger and protrudes from the elongated hollow tube through the slot and is translatable along the slot to move the plunger and compress the spring member. Upon release of the handle, the compressed spring member propels the plunger to apply an impact force to a projection welded component.

20 Claims, 5 Drawing Sheets

(56) References Cited

U.S. PATENT DOCUMENTS 6,418,628 B1 * 7/2002 Steingass ............... B60R 22/32
 30/367
9,375,589 B1 * 6/2016 Goodman .............. A62B 3/005

FOREIGN PATENT DOCUMENTS

CN 204203000 U 3/2015
CN 104819902 A 8/2015

* cited by examiner

QUALITY INSPECTION TOOL FOR PROJECTION WELDED FASTENERS

TECHNICAL FIELD

The present disclosure relates generally to mechanical inspections tools used in the automotive and metallurgical industries. More particularly, the present disclosure relates to a quality inspection tool and methods for the non-destructive testing of automotive projection welded fasteners and the like.

BACKGROUND

During the manufacturing of automobiles and automotive parts, components thereof are often metallurgically bonded together, such as by projection welding. In particular, components including fasteners, such as threaded or unthreaded nuts, are metallurgically bonded to other components. For example, an unthreaded nut will typically later be threaded by a screw when the screw is fastened to the nut and the attached component.

Testing is often performed to ensure the quality of the metallurgical bonds between such components. One of three methods are typically used for testing the quality of the metallurgical bond for a fastener, such as a projection welded fastener, bonded to another component. These methods include a push-out test, a torque test, and an impact test.

The push-out test is a destructive test that drives a rod transverse to a surface of the component that the fastener is bonded to, which is driven through the metallurgical bond to test the strength thereof. The rod is typically driven using hydraulic pressure, and thus, the push-out test typically requires a machine for supplying hydraulic pressure and a structure that guides the rod through the metallurgical bond.

For the torque test, a torque wrench is typically used to apply a set amount of torque to the fastener. The tester sets the torque wrench with the set amount of force to be applied, places the torque wrench on the fastener, and applies the force to the handle of the torque wrench until the torque wrench identifies that the set amount of torque is being applied by the tester. However, the torque test can give false result, with a specified torque approving an otherwise undersized weld.

For the impact test, a tester typically impacts the fastener with a hammer. The impact is typically at the top of the head of the fastener, normal to the surface of the component that the fastener is metallurgically bonded to. However, each individual tester is going to strike the fastener with a different amount of force. Further, each individual strike by the tester is not going to be the same amount of force. Thus, the accuracy and reliability of the impact test are difficult to determine since the exact force applied in each instance of the impact test is unknown.

The above-described background relating to the inspection of projection welded fasteners and the like is merely intended to provide a contextual overview of some current issues and is not intended to be exhaustive. Other contextual information may become apparent to those of ordinary skill in the art upon review of the following description of exemplary embodiments.

SUMMARY

The present disclosure generally provides a handheld quality inspection tool for projection welded components. The handheld quality inspection tool is adapted to be aligned with the projection welded component and to apply a normative impact stroke to the projection welded component. In particular, a plunger is connected to a spring member and a handle. The handle is movable by a tester applying a force thereto, which compresses the spring a known amount, such that upon release of the handle, the spring member propels the plunger that applies a known impact force to the projection welded component, which improves the reliability and safety of the test.

In one exemplary embodiment, the present disclosure provides a handheld quality inspection tool for projection welded components. The handheld quality inspection tool includes an elongated hollow tube, an end flange, a spring support, a spring member, a plunger, and a handle. The elongated hollow tube defines a slot along a length direction thereof. The end flange defines an opening connected to an end portion of the elongated hollow tube and is adapted to directly or indirectly abut one of the projection welded components. The spring support is connected to an opposite end portion of the elongated hollow tube. The spring member is disposed within the elongated hollow tube and connected to the spring support. The plunger is disposed in the elongated hollow tube and connected to the spring member opposite the spring support. The handle is connected to the plunger and protrudes from the elongated hollow tube through the slot and adapted to, when receiving a force, translate along the slot and move the plunger within the elongated hollow tube in the length direction to compress the spring member. Upon release of the force from the handle, the spring member is adapted to propel the plunger towards the end flange and apply an impact force to one of the projection welded components. Optionally, upon release of the force from the handle, the spring member causes the plunger to impact a threaded or unthreaded blank (i.e., insert, sacrificial screw, or the like) that is coupled to the welded component(s) and disposed within the opening defined by the end flange.

In one embodiment of the handheld quality inspection tool, a length of the slot is selected to bound compression of the spring member between a minimum compression before the force is applied to the handle and a maximum compression after the force is applied to the handle, thereby bounding the impact force applied to the one of the projection welded components by the plunger when the force is released from the handle. In another embodiment of the handheld quality inspection tool, the elongated hollow tube comprises an internally-threaded section at the opposite end portion adjacent to the spring support. The spring support comprises an externally-threaded cylinder structure mated to the internally-threaded section. And the spring support is adapted to translate in the length direction relative to the elongated hollow tube to modify a maximum impact force appliable by the handheld quality inspection tool. Optionally, the handheld quality inspection tool further includes a grip connected to the spring support, protruding from the elongated hollow tube, and adapted to transfer a torque applied at the grip to the spring support for translating the spring support in the length direction relative to the elongated hollow tube. Optionally, the spring support defines a screw drive adapted to interface with a mating tool adapted to apply a torque to the spring support for translating the spring support in the length direction relative to the elongated hollow tube. In a further embodiment of the handheld quality inspection tool, the elongated hollow tube comprises an externally-threaded section at the end of the elongated hollow tube, and the end flange comprises an internally-threaded section mated with the externally-threaded section of the elongated hollow tube.

In another exemplary embodiment, the present disclosure provides a method for verifying a weld quality of a projection welded component. The method includes aligning a handheld quality inspection tool with the projection welded component such that the projection welded component directly or indirectly abuts an end of the handheld quality inspection tool. The method also includes applying a normative impact stroke to the projection welded component with the handheld quality inspection tool.

In one embodiment of the method, the handheld quality inspection tool includes an elongated hollow tube, an end flange, a spring support, a spring member, a plunger, and a handle. The elongated hollow tube defines a slot along a length direction thereof. The end flange defines an opening connected to an end portion of the elongated hollow tube. The spring support is connected to an opposite end portion of the elongated hollow tube. The spring member is disposed within the elongated hollow tube and is connected to the spring support. The plunger is disposed in the elongated hollow tube and is connected to the spring member opposite the spring support. The handle is connected to the plunger and is protruding from the elongated hollow tube through the slot. The step of aligning the handheld quality inspection tool with the projection welded component such that the projection welded component directly or indirectly abuts the end of the handheld quality inspection tool includes locating the end flange to directly or indirectly abut the projection welded component. And the step of applying the normative impact stroke to the projection welded component with the handheld quality inspection tool includes translating the handle along the slot and moving the plunger within the elongated hollow tube in the length direction to compress the spring member and releasing the handle such that the spring member propels the plunger towards the end flange and applies an impact force to the projection welded component. Optionally, upon releasing the handle, the spring member causes the plunger to impact a threaded or unthreaded blank that is coupled to the welded component(s) and disposed within the opening defined by the end flange.

Optionally, the elongated hollow tube comprises an internally-threaded section at the opposite end portion adjacent to the spring support. The spring support comprises an externally-threaded cylinder structure mated to the internally-threaded section. And the method further comprises calibrating the handheld inspection tool by rotating the spring support such that the spring support translates in the length direction relative to the elongated hollow tube. Optionally, the handheld inspection tool further comprises a grip connected to the spring support, protruding from the elongated hollow tube, and calibrating the handheld inspection tool includes applying a torque to the spring support via the grip to translate the spring support in the length direction relative to the elongated hollow tube. Optionally, the spring support defines a screw drive, and calibrating the handheld inspection tool includes mating a tool with the screw drive and applying a torque to the spring support via the tool to translate the spring support in the length direction relative to the elongated hollow tube. Optionally, the method further includes selecting the end flange from a plurality of end flanges and connecting the end flange to the elongated hollow tube by mating an internal-threaded section of the end flange to an external-threaded section of the elongated hollow tube.

BRIEF DESCRIPTION OF THE DRAWINGS

The present disclosure is illustrated and described herein with reference to the various drawings, in which like reference numbers are used to denote like system components/ method steps, as appropriate, and in which.

DESCRIPTION OF EXEMPLARY EMBODIMENTS

The present disclosure relates to a handheld quality inspection tool for projection welded components and methods for performing inspections of projection welded components using the handheld quality inspection tool. Again, the handheld quality inspection tool is adapted to be aligned with the projection welded component and to apply a normative impact stroke to the projection welded component. In particular, a plunger is connected to a spring member and a handle. The handle is movable by a tester applying a force thereto, which compresses the spring a known amount, such that upon release of the handle, the spring member propels the plunger that applies a known impact force to the projection welded component.

Due to the configuration of the handheld quality inspection tool, the tester is able to apply a normative and known force to each projection welded component tested, which ensures the effectiveness of the impact test. Also, the handheld quality inspection tool is relatively small compared to what is required by a push-out testing device, and as such, is easily moved from one projection welded component to the next, allowing for quick testing of multiple components. Further, since the tester is not driving the force of the plunger during the impact of the plunger with the projection welded component (the force is supplied by the compressed spring), there is no danger of the hand of the tester releasing into the component, and the chances of injury to the tester during the testing of the metallurgical bond is reduced.

Figure 1:
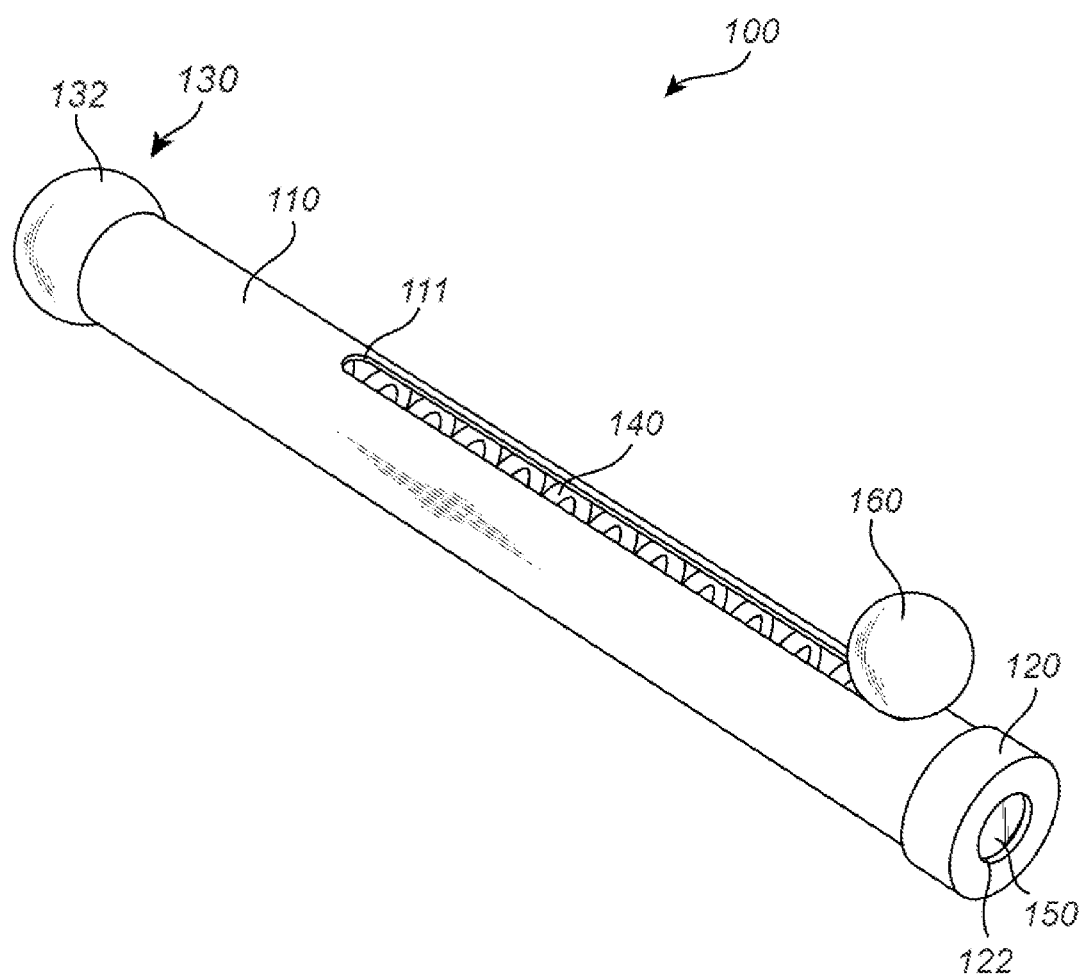
FIG. 1 is a perspective view of an exemplary embodiment of a handheld quality inspection tool for projection welded components of the present disclosure.
Figure 2:
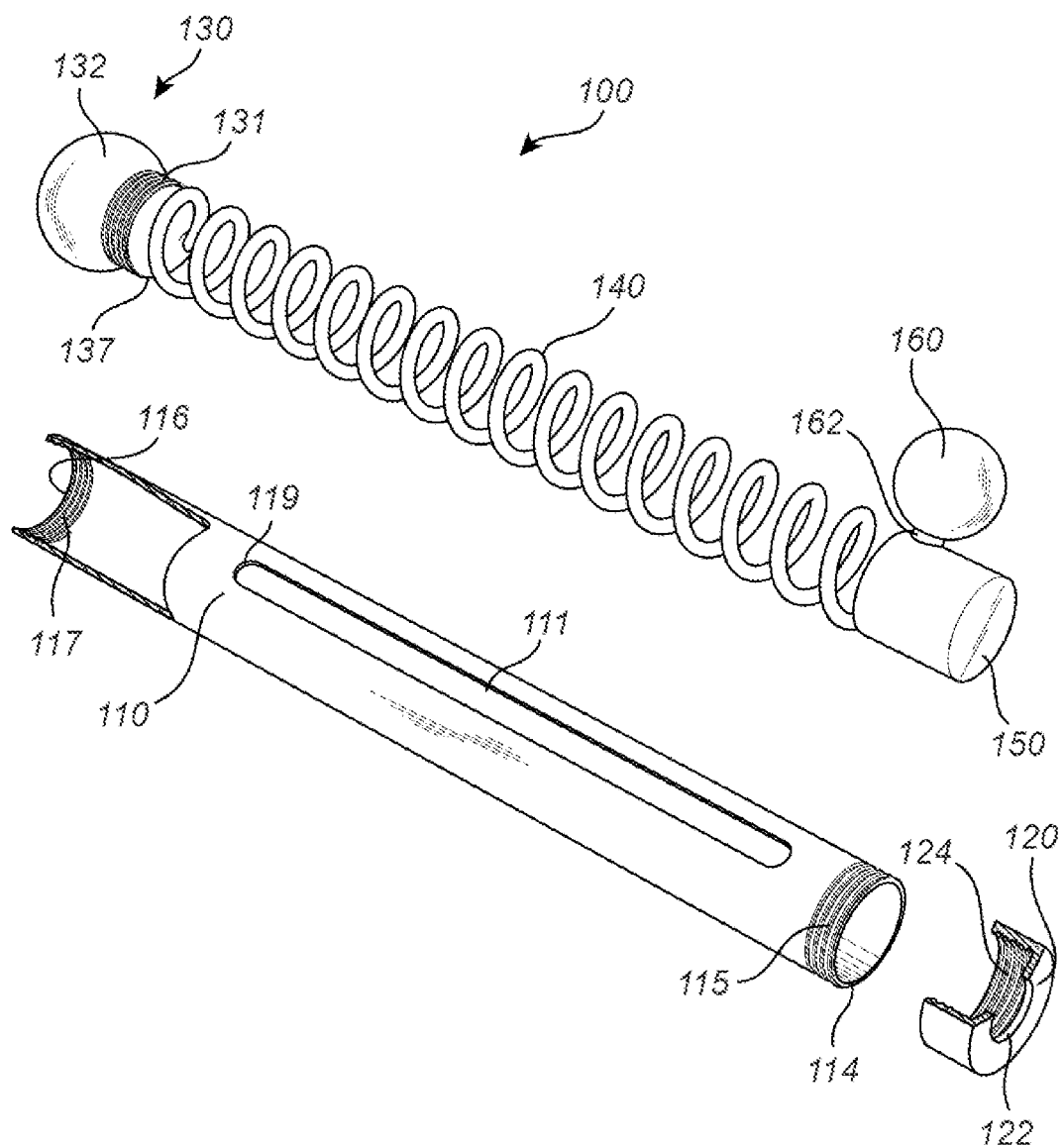
FIG. 2 is a perspective exploded view of the handheld quality inspection tool for projection welded components of FIG. 1 with portions thereof cutaway.

FIG. 1 is a perspective view of an exemplary embodiment of a handheld quality inspection tool 100 for projection welded components of the present disclosure. FIG. 2 is a perspective exploded view of the handheld quality inspection tool 100 for projection welded components of FIG. 1 with portions thereof cutaway. Referring to FIGS. 1 and 2, in embodiments, the handheld quality inspection tool includes an elongated hollow tube 110, an end flange 120, a spring support 130, a spring member 140, a plunger 150, and a handle 160.

The elongated hollow tube 110 defines a slot 111 along a length direction thereof. Optionally, a length of the slot 111 is selected to bound compression of the spring member 140 between a minimum compression before a force is applied to the handle 160 and a maximum compression after the force is applied to the handle 160. This bounds the impact force applied to a projection welded component by the plunger 150 when the force is released from the handle 160. As shown in FIG. 2, the elongated hollow tube 110 optionally includes an externally-threaded section 115 at the end portion 114 of the elongated hollow tube 110, and the elongated hollow tube 10 optionally includes an internally-threaded section 117 at the opposite end portion 116 adjacent to the spring support 130. The opposite end portion 116 is positioned distal to the end portion 114.

The end flange 120 defines an opening 122 connected to the end portion 122 of the elongated hollow tube 110 and is adapted to abut one of the projection welded components. More specifically, the opening 122 of the end flange 120 is adapted to receive an unthreaded or threaded blank that is engaged with one of the projection welded components (such as an unthreaded or threaded nut welded to a panel), providing a force transfer path between the spring member 140 and plunger 150 and that projection welded component. Optionally, the end flange 120 includes an internally-threaded section 124 mated with the externally-threaded section 115 of the elongated hollow tube 110. Alternatively, the end flange 120 is metallurgically bonded to the elongated hollow tube 110. Optionally, the opening 122 is sized based on the projection welded component to be tested. Further, in some embodiments, the handheld quality inspection tool 100 includes multiple end portions 120 and the end portion 120 is selected based on the projection welded component to be tested. In embodiments, the projection welded component is a fastener, such as an unthreaded nut.

The spring support 130 is connected to the opposite end portion 116 of the elongated hollow tube 110. The spring support 130 includes a cylindrical structure 131 mated to the other end 116 of the elongated hollow tube 110. Optionally, the cylindrical structure 131 includes an externally-threaded cylinder structure 137, and the externally-threaded cylinder structure 137 is mated to the internally-threaded section 117 of the elongated hollow tube 110. The spring support 130 is adapted to translate in the length direction relative to the elongated hollow tube 110 to modify a maximum impact force appliable by the handheld quality inspection tool 100. In particular, by rotating the spring support 130, the mated externally-threaded cylinder structure 137 of the spring support 130 and internally-threaded section 117 of the elongated hollow tube 110 the spring support 130 is threaded further into or out of the elongated hollow tube 110, which causes the translation of the spring support 130 relative to the elongated hollow tube 110.

In embodiments, the spring support 130 includes a grip 132 connected to the cylindrical structure 131. The grip 132 protrudes from the elongated hollow tube 110 and is adapted to transfer a torque applied at the grip 132 to the cylindrical structure 131 for translating the spring support 130 in the length direction relative to the elongated hollow tube 110. Alternatively, the grip 132 is a separate component connected to the spring support 130.

In some embodiments, the spring support 130 is metallurgically bonded to the elongated hollow tube 110.

The spring member 140 is disposed within the elongated hollow tube 110 and is connected to the spring support 130, such as at an end of the cylindrical structure 131. The spring member 140 is a resilient device that is compressible along the length of the elongated hollow tube 110. In embodiments, the spring member 140 is a helical metal coil.

The plunger 150 is disposed in the elongated hollow tube 110 and is connected to the spring member 140 opposite the spring support 130. When the handheld quality inspection tool 100 is in an equilibrium condition, the plunger 150 is positioned adjacent to or positioned partially within the end flange 120.

The handle 160 is connected to the plunger 150 and protrudes from the elongated hollow tube 110 through the slot 111. The handle 160 is adapted to, when receiving a force, translate along the slot 111 and move the plunger 160 within the elongated hollow tube 110 in the length direction to compress the spring member 140, such that, upon release of the force from the handle 160, the spring member 140 is adapted to propel the plunger 150 towards the end flange 120 and apply an impact force to one of the projection welded components.

In embodiments, the handle 160 includes a connector 162 that connects the handle 160 to the plunger 150. Optionally, the handle 160 includes an externally-threaded end that mates with an internally-threaded hole in the plunger 150.

Figure 3:
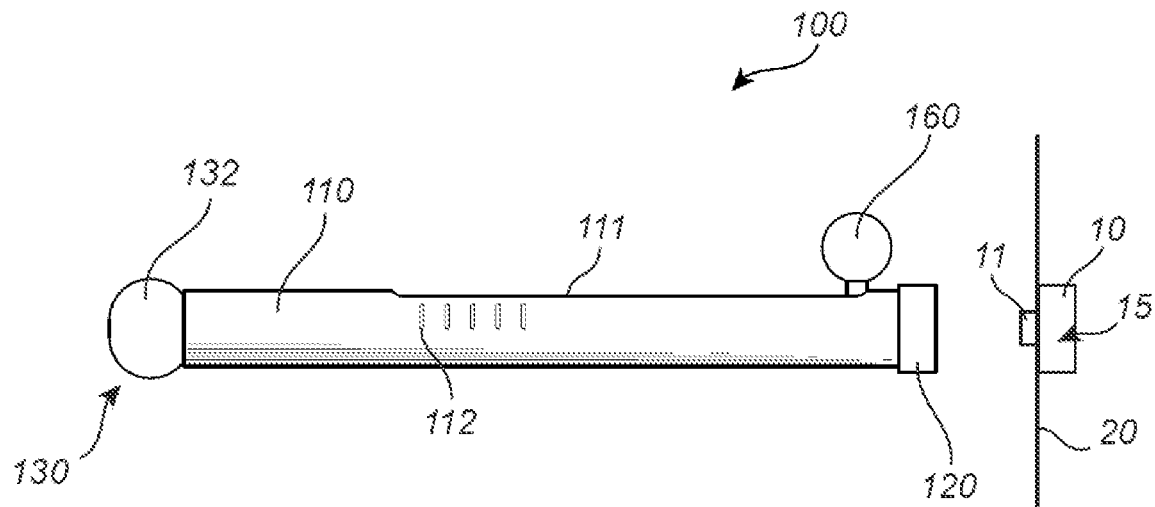
FIG. 3 is a side perspective view of the handheld quality inspection tool for projection welded components of FIG. 1 adjacent to the projection welded component and including multiple markings.

FIG. 3 is a side perspective view of the handheld quality inspection tool 100 for projection welded components 10 of FIG. 1 adjacent to the projection welded component 10 and coupled blank 11 and including multiple markings. As described above, the handle 160 is translated along the slot 111 to compress the spring member 140, such that upon release, the spring member 140 propels the plunger 150 toward the end flange 120 to apply an impact force to the blank 11 and projection welded component 10. This impact force tests the quality of the metallurgical bond 15 between the projection welded component 10 and the other component 20.

In embodiments, the handheld inspection tool 100 further includes at least one marking 112 applied to an external surface of the elongated hollow tube 110 adjacent to the slot 111. The markings 112 each identify a position for the handle 160 and plunger 150 from where a known impact force is applied to the projection welded component 10 when the handle 160 is released at the marking 112. In embodiments, each marking 112 is positioned on the elongated hollow tube 110 based on a pre-determined standard force for testing the quality of the metallurgical bond 15.

Figure 4:
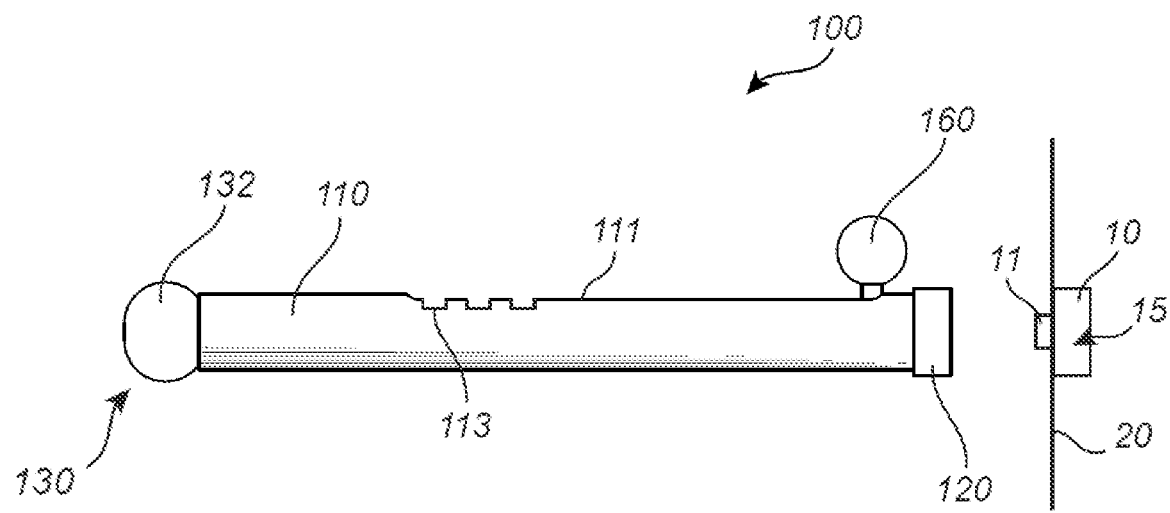
FIG. 4 is a side perspective view of the handheld quality inspection tool for projection welded components of FIG. 1 adjacent to the projection welded component and including multiple notches.

FIG. 4 is a side perspective view of the handheld quality inspection tool 100 for projection welded components 10 of FIG. 1 adjacent to the projection welded component 10 and coupled blank 11 and including multiple notches 113. In embodiments, the handheld inspection tool 100 further includes at least one notch 113 defined by the elongated hollow tube adjacent to the slot 111. Each notch 113 is contiguous to the slot 111 and extends therefrom. Each notch 113 provides detent position for the handle 160 and plunger 150 from where a known impact force is applied to the blank 11 and projection welded component 10 when the handle 160 is released at the notch 113.

Figure 5:
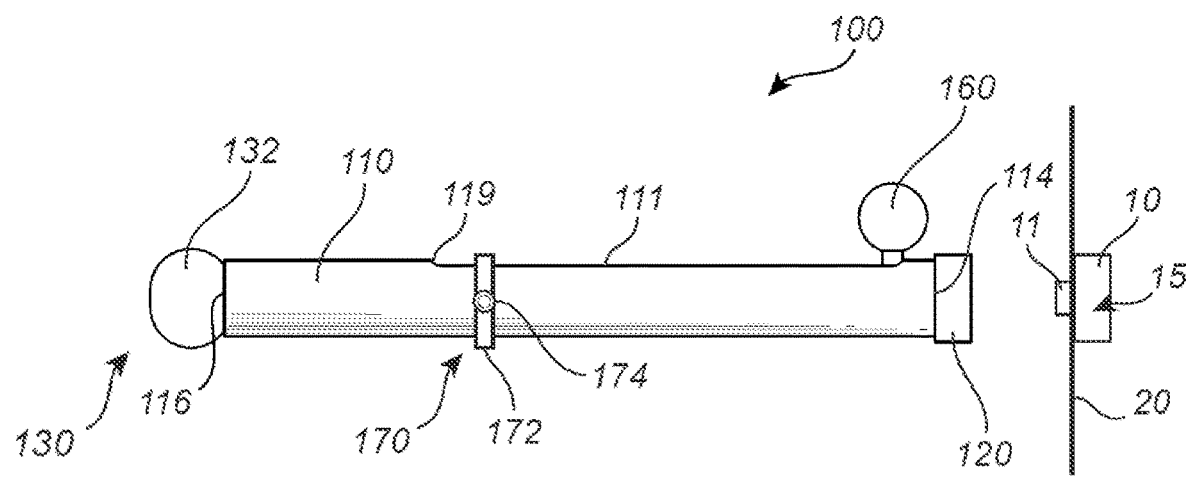
FIG. 5 is a side perspective view of the handheld quality inspection tool for projection welded components of FIG. 1 adjacent to the projection welded component and including a slider.

FIG. 5 is a side perspective view of the handheld quality inspection tool 100 for projection welded components 10 of FIG. 1 adjacent to the projection welded component 10 and coupled blank 11 and including a slider 170.

In embodiments, the handheld quality inspection tool 100 further includes a slider 170 positioned between the end portions 114, 116 of the elongated hollow tube110. The slider 170 includes a ring 172 adapted to move along the length direction of the elongated hollow tube 110 and a set screw 174 adapted to secure the ring 172 relative to the elongated hollow tube 110. The slider 170 is adapted to obstruct the handle 160 from being moved to the end portion 119 of the slot 111 to control the impact force appliable by the handheld quality inspection tool 100. In embodiments, the positioning of the slider 170 is guided by the markings 112 of FIG. 3 described above. In particular, the set screw 174 is released, which allows to the ring 172 to move in the length direction of the elongated hollow tube 110. Once the ring 172 is in a desired position, such as aligning with one of the markings 112, the set screw 174 is positioned to secure the ring 172 in position relative to the elongated hollow tube 110.

Figure 6:
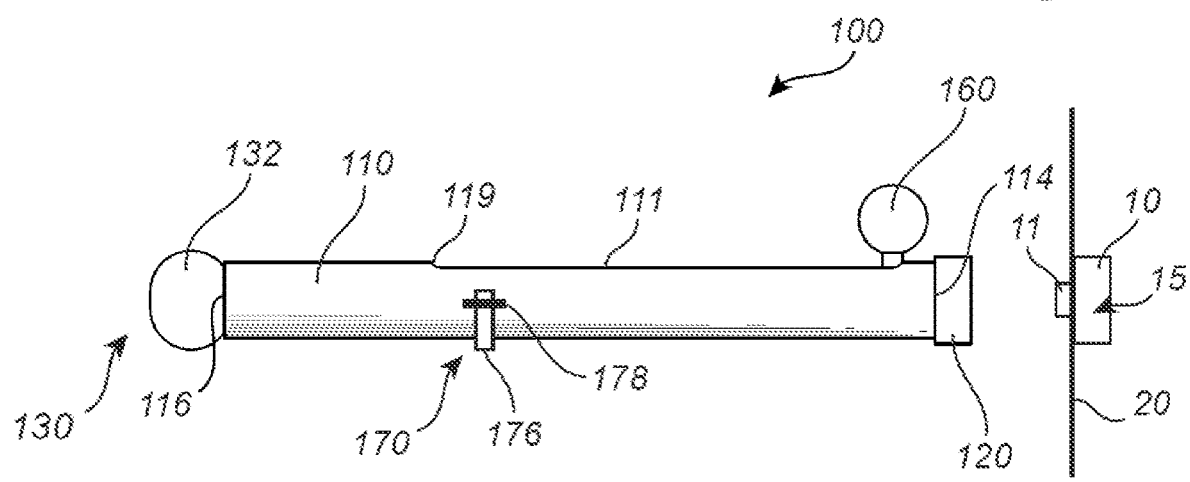
FIG. 6 is a side perspective view of the handheld quality inspection tool for projection welded components of FIG. 1 adjacent to the projection welded component and including a slider in a first configuration.
Figure 7:
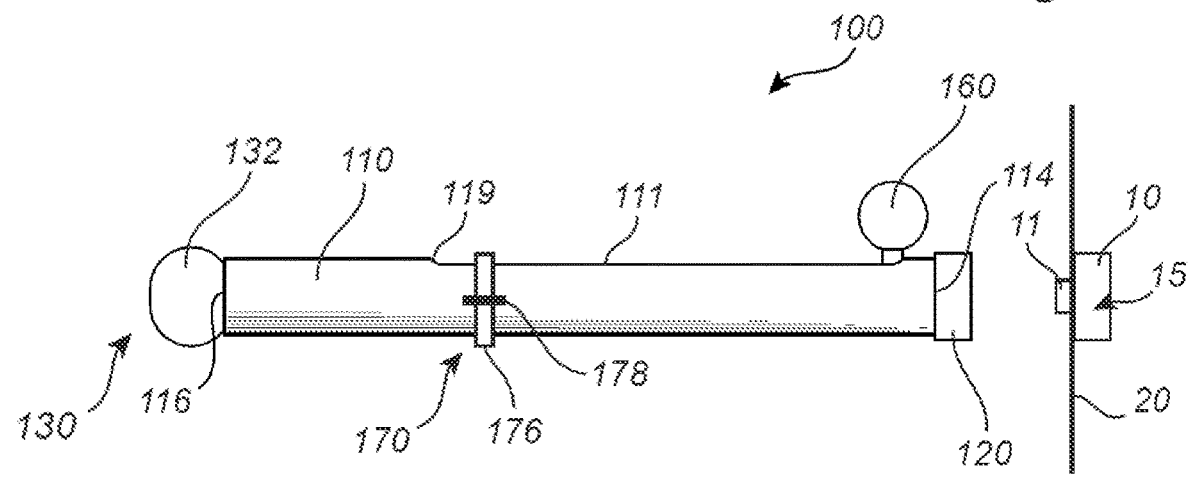
FIG. 7 is a side perspective view of the handheld quality inspection tool for projection welded components of FIG. 6 adjacent to the projection welded component and including a slider in a second configuration.

FIG. 6 is a side perspective view of the handheld quality inspection tool 100 for projection welded components 10 of FIG. 1 adjacent to the projection welded component 10 and coupled blank 11 and including a slider 170 in a first configuration. FIG. 7 is a side perspective view of the handheld quality inspection tool 100 for projection welded components 10 of FIG. 6 adjacent to the projection welded component 10 and coupled blank and including the slider 170 in a second configuration.

In the embodiment shown in FIGS. 6 and 7, the slider 170 is fixed along the length direction between the ends 114 and 116 of the elongated hollow tube 100 and adapted to move in one of a circumferential direction and an orthogonal direction relative to the elongated hollow tube 110 from a first configuration positioning the slider 170 adjacent to the slot 111, as shown in FIG. 6, to a second configuration positioning the slider 170 over the slot 111, as shown in FIG. 7, to obstruct the handle 160 from being moved to the end portion 119 of the slot 111 to control the impact force appliable by the handheld quality inspection tool 100. The slider 170 includes a sliding portion 176 and one or more brackets 178. The sliding portion 176 is slidably coupled to the elongated hollow tube 110 by the one or more brackets 178. The sliding portion 178 moves relative to the one or more brackets 178 in the one of the circumferential direction and the orthogonal direction of the elongated hollow tube 110 between the first configuration and the second configuration.

Figure 8:
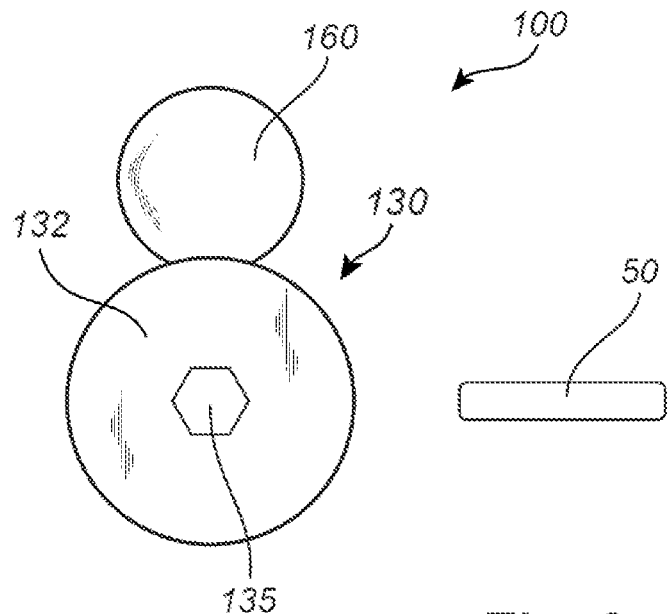
FIG. 8 is a top perspective view of the handheld quality inspection tool for projection welded components of FIG. 1 including a screw drive.

FIG. 8 is a top perspective view of the handheld quality inspection tool 100 for projection welded components of FIG. 1 including a screw drive 135. In embodiments, the spring support 130 defines a screw drive 135 adapted to interface with a mating tool 50. The mating tool 50 is adapted to mate with the screw drive 135 and apply a torque to the spring support 130 for translating the spring support 130 in the length direction relative to the elongated hollow tube 110 as described above. Optionally, the screw drive is formed in one of the cylindrical structure 131 and the grip 132 of the spring support 130. In embodiments, the screw drive 135 is one of a slotted drive, a cruciform drive, a square drive, an internal hex drive, and the like. Optionally, a non-standard proprietary screw drive is used to prevent tampering with the handheld quality inspection tool 100.

Figure 9:
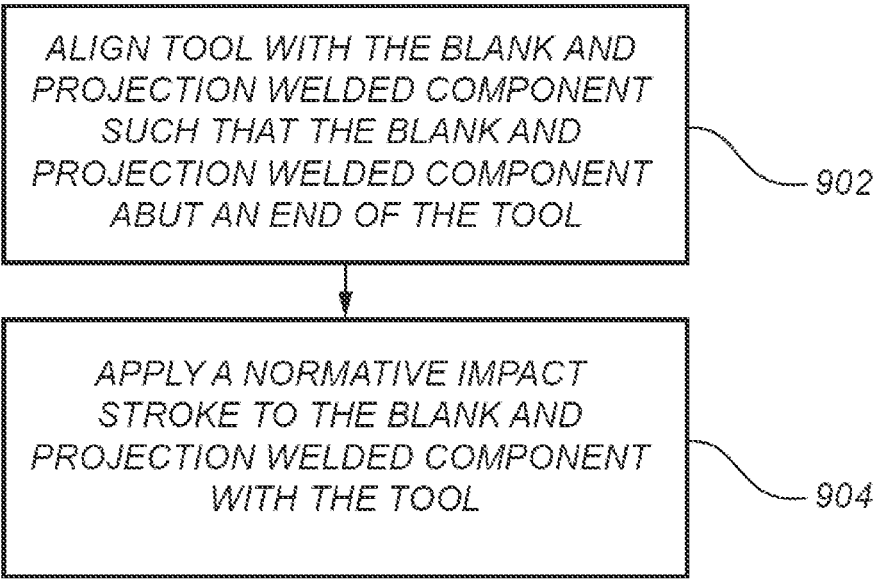
FIG. 9 is a flowchart of a method for verifying a weld quality of a projection welded component.

FIG. 9 is a flowchart of a method 900 for verifying a weld quality of a projection welded component 10. The method 900 includes aligning a handheld quality inspection tool 100 with the projection welded component(s) 10 such that the projection welded component(s) 10 abut an end of the handheld quality inspection tool at step 902. This is accomplished by first coupling an unthreaded or threaded blank 11 (i.e., an insert, a sacrificial screw, or the like) to the projection welded component 10 and then disposing the opening 122 of the flange 120 about the blank 11. The blank 11 thus forms a linking structure for transferring the delivered force from the spring member 140 and plunger 150 to the projection welded component 10. The method 900 also includes applying a normative impact stroke to the blank 11 and projection welded component 10 with the handheld quality inspection tool at step 904.

In embodiments, the handheld quality inspection tool 100 of the method 900 includes a combination of the features in the embodiments described above. Optionally, step 902 includes locating the end flange 120 to encompass the blank 11 and abut the projection welded component(s) 10, and step 904 includes translating the handle 160 along the slot 111 and moving the plunger 150 within the elongated hollow tube 110 in the length direction to compress the spring member 140 and releasing the handle 160 such that the spring member 140 propels the plunger 150 towards the end flange 120 and applies an impact force to the blank 11 and projection welded component 10.

Optionally, translating the handle 160 along the slot 111 includes translating the handle to an end 119 of the slot such that a maximum compression is applied to the spring member 140 by the plunger 150 and the impact force is a maximum force appliable by the handheld quality inspection tool 100.

In embodiments, the method 900 also includes calibrating the handheld inspection tool 100 by rotating the spring support 130 such that the spring support 130 translates in the length direction relative to the elongated hollow tube 110. Optionally, calibrating the handheld inspection tool 100 includes applying a torque to the spring support 130 via the grip 132 to translate the spring support 130 in the length direction relative to the elongated hollow tube 110. Optionally, calibrating the handheld inspection tool 100 includes mating a tool 50 with the screw drive 135 and applying a torque to the spring support 130 via the tool 50 to translate the spring support 130 in the length direction relative to the elongated hollow tube 110.

In embodiments, the handheld inspection tool 100 includes multiple end flanges 120, which are sized, including the opening 122, based on a size of the projection welded component 10. The method 900 further includes selecting the end flange 120 from multiple end flanges 120 and connecting the end flange 120 to the elongated hollow tube 110 by mating the internally-threaded section 125 of the end flange 120 to an externally-threaded section 115 of the elongated hollow tube 110.

Optionally, translating the handle 160 along the slot 111 and moving the plunger 150 within the elongated hollow tube 110 in the length direction to compress the spring member 140 includes translating the handle 160 to align with a marking 112 on the elongated hollow tube110. As described above, the marking 112 is adapted to identify a position for the handle 160 and the plunger 150 from where a known impact force is applied to the projection welded component 10 when the handle 160 is released at the marking 112.

Optionally, translating the handle 160 along the slot 111 and moving the plunger 150 within the elongated hollow tube 110 in the length direction to compress the spring member 140 includes translating the handle 160 to a notch 113 adjacent to the slot 111. As described above, notch 113 is a detent position for the handle 160 where a known impact force is applied to the projection welded component when the handle 160 is released at the notch 113.

In embodiments, the method further includes positioning a slider 170 to obstruct at least a portion of the slot 111 such that the handle 160 is prevented from moving to an end 119 of the slot 111. Further, translating the handle 160 along the slot 111 and moving the plunger 150 within the elongated hollow tube 110 in the length direction to compress the spring member 140 includes translating the handle 160 to the slider 170. Optionally, the slider 170 includes the ring 172 and set screw 174, as shown in FIG. 5, or the movable arm 176 and bracket 178, as shown in FIG. 6. Other configurations of sliders 170 are also contemplated.

As discussed above, the handheld quality inspection tool 100 is adapted to be aligned with the projection welded component 10 and to apply a normative impact stroke to the projection welded component 10. In particular, the plunger 150 is connected to a spring member 150 and a handle160. The handle is movable when a force is applied thereto, which upon movement, causes the plunger 150 to compress the spring member 140. Based on at least one of a length of the slot 111, a location of the marking 112, the location of a notch 113, or a position of the slider 170, upon release of the handle 160, the spring member 140 propels the plunger 150 to apply an impact force to the projection welded component 10.

The impact force applied by a normative impact stroke since the impact stroke is measurable relative to one of a length of the slot 111, a location of the marking 112, the location of a notch 113, or a position of the slider 170. Thus, by use of the handheld quality inspection tool 100 as described herein, a repeatable impact stroke, with a repeatable impact force, is attainable, which improves the accuracy and validity of an impact test for projection welded components.

Since the handheld quality inspection tool 100 is relatively small the handheld quality inspection tool 100 is portable and easily moved from one projection welded component 10 to the next, allowing for quick testing of multiple projection welded components 10. Further, since the tester is not driving the force of the plunger during the impact stroke, the dangers associated with other testing methods, such as the torque testing method, are avoided.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A handheld quality inspection tool for a welded component, comprising:
    an elongated hollow tube defining a slot along a length thereof;
    an end flange defining an opening connected to an end of the elongated hollow tube and adapted to directly or indirectly abut the welded component;
    a spring support connected at an opposite end of the elongated hollow tube;
    a spring member disposed within the elongated hollow tube and connected to the spring support;
    a plunger disposed in the elongated hollow tube and connected to the spring member opposite the spring support; and
    a handle connected to the plunger and protruding from the elongated hollow tube through the slot and adapted to, when receiving a force, translate along the slot and move the plunger within the elongated hollow tube lengthwise to compress the spring member, such that, upon release of the force from the handle, the spring member propels the plunger towards the end flange and applies an impact force to the welded component by the plunger impacting the welded component directly or by the plunger impacting a blank that is coupled to the welded component.

2. The handheld quality inspection tool of claim 1, wherein, upon release of the force from the handle, the spring member causes the plunger to impact a threaded or unthreaded blank that is coupled to the welded component and disposed within the opening defined by the end flange.

3. The handheld quality inspection tool of claim 1, wherein a length of the slot is selected to bound compression of the spring member between a minimum compression before the force is applied to the handle and a maximum compression after the force is applied to the handle, thereby bounding the impact force applied to the welded component by the plunger when the force is released from the handle.

4. The handheld quality inspection tool of claim 1, wherein the elongated hollow tube comprises an internally-threaded section at the opposite end adjacent to the spring support, the spring support comprises an externally-threaded cylinder structure mated to the internally-threaded section, and the spring support is adapted to translate along the length of the elongated hollow tube to modify a maximum impact force appliable by the handheld quality inspection tool.

5. The handheld quality inspection tool of claim 3, further comprising a grip connected to the spring support, protruding from the elongated hollow tube, and adapted to transfer a torque applied at the grip to the spring support for translating the spring support along the length of the elongated hollow tube.

6. The handheld quality inspection tool of claim 3, wherein the spring support defines a screw drive adapted to interface with a mating tool adapted to apply a torque to the spring support for translating the spring support along the length of the elongated hollow tube.

7. The handheld quality inspection tool of claim 1, wherein the elongated hollow tube comprises an externally-threaded section at the end of the elongated hollow tube, and the end flange comprises an internally-threaded section mated with the externally-threaded section of the elongated hollow tube.

8. The handheld quality inspection tool of claim 1, further comprising a plurality of markings applied to an external surface of the elongated hollow tube adjacent to the slot adapted to identify a plurality of positions for the handle and plunger from where a known impact force is applied to the welded component when the handle is released at each of the plurality of markings.

9. The handheld quality inspection tool of claim 1, further comprising a plurality of notches defined by the elongated hollow tube adjacent to the slot adapted to provide a plurality of detent positions for the handle and plunger from where a known impact force is applied to the welded component when the handle is released at each of the plurality of notches.

10. The handheld quality inspection tool of claim 1, further comprising a slider positioned between the end portions of the elongated hollow tube, the slider including a ring adapted to move along the length of the elongated hollow tube and a set screw adapted to secure the ring relative to the elongated hollow tube, and the slider adapted to obstruct the handle from being moved to the end of the slot to control the impact force appliable by the handheld quality inspection tool.

11. The handheld quality inspection tool of claim 1, further comprising a slider fixed along the length direction between the ends of the elongated hollow tube and adapted to move in one of a circumferential direction and an orthogonal direction relative to the elongated hollow tube from a first configuration positioning the slider adjacent to the slot and a second configuration positioning the slider over the slot to obstruct the handle from being moved to the end of the slot to control the impact force appliable by the handheld quality inspection tool.

12. A method for verifying a weld quality of a welded component, the method comprising:
aligning a handheld quality inspection tool with the welded component such that the welded component directly or indirectly abuts an end of the handheld quality inspection tool; and
applying a normative impact stroke to the welded component with the handheld quality inspection tool by a plunger of the handheld quality inspection tool impacting the welded component directly or by the plunger of the handheld quality inspection tool impacting a blank that is coupled to the welded component.

13. The method of claim 12, wherein the handheld quality inspection tool comprises:
an elongated hollow tube defining a slot along a length thereof;
an end flange defining an opening connected to an end of the elongated hollow tube;
a spring support connected at an opposite end of the elongated hollow tube;
a spring member disposed within the elongated hollow tube and connected to the spring support;
the plunger disposed in the elongated hollow tube and connected to the spring member opposite the spring support; and
a handle connected to the plunger and protruding from the elongated hollow tube through the slot, wherein
aligning the handheld quality inspection tool with the welded component such that the welded component directly or indirectly abuts the end of the handheld quality inspection tool comprises locating the end flange to directly or indirectly abut the welded component, and
applying the normative impact stroke to the welded component with the handheld quality inspection tool comprises translating the handle along the slot and moving the plunger within the elongated hollow tube lengthwise to compress the spring member and releasing the handle such that the spring member propels the plunger towards the end flange and applies an impact force to the welded component by the plunger impacting the welded component directly or by the plunger impacting the blank that is coupled to the welded component.

14. The method of claim 13, wherein, upon releasing the handle, the spring member causes the plunger to impact a threaded or unthreaded blank that is coupled to the welded component and disposed within the opening defined by the end flange.

15. The method of claim 13, wherein translating the handle along the slot comprises translating the handle to an end of the slot such that a maximum compression is applied to the spring member by the plunger and the impact force is a maximum force appliable by the handheld quality inspection tool.

16. The method of claim 13, wherein the elongated hollow tube comprises an internally-threaded section at the opposite end adjacent to the spring support, the spring support comprises an externally-threaded cylinder structure mated to the internally-threaded section, and the method further comprises calibrating the handheld inspection tool by rotating the spring support such that the spring support translates along the length of the elongated hollow tube.

17. The method of claim 13, wherein the handheld inspection tool further comprises a grip connected to the spring support, protruding from the elongated hollow tube, and calibrating the handheld inspection tool comprises applying a torque to the spring support via the grip to translate the spring support along the length of the elongated hollow tube.

18. The method of claim 13, wherein the spring support defines a screw drive, and calibrating the handheld inspection tool comprises mating a tool with the screw drive and applying a torque to the spring support via the tool to translate the spring support along the length of the elongated hollow tube.

19. The method of claim 13, wherein translating the handle along the slot and moving the plunger within the elongated hollow tube along the length thereof to compress the spring member comprises translating the handle to align with a position on the elongated hollow tube, and wherein the position is adapted to identify a location for the handle and the plunger from where a known impact force is applied to the welded component when the handle is released at the marking.

20. A handheld quality inspection tool for a welded component, comprising:
an elongated hollow tube defining a slot along a length thereof;
an end flange defining an opening connected to an end of the elongated hollow tube and adapted to abut a blank contacting the welded component;
a spring support connected at an opposite end of the elongated hollow tube;
a spring member disposed within the elongated hollow tube and connected to the spring support;
a plunger disposed in the elongated hollow tube and connected to the spring member opposite the spring support; and
a handle connected to the plunger and protruding from the elongated hollow tube through the slot and adapted to, when receiving a force, translate along the slot and move the plunger within the elongated hollow tube lengthwise to compress the spring member, such that, upon release of the force from the handle, the spring member propels the plunger towards the end flange and applies an impact force to the blank and the welded component by the plunger impacting the blank contacting the welded component.

* * * * *